US012734243B2

(12) United States Patent
Zhang et al.

(10) Patent No.: US 12,734,243 B2
(45) Date of Patent: Sep. 15, 2026

(54) POLYPEPTIDE DERIVATIVE AND PREPARATION METHOD THEREOF

(71) Applicant: NINGBO KUNPENG BIOTECH CO., LTD., Ningbo (CN)

(72) Inventors: Zhenshan Zhang, Ningbo (CN); Song Wu, Ningbo (CN); Huiling Liu, Ningbo (CN); Wei Chen, Ningbo (CN)

(73) Assignee: NINGBO KUNPENG BIOTECH CO., LTD., Ningbo (CN)

( * ) Notice: Subject to any disclaimer, the term of this patent is extended or adjusted under 35 U.S.C. 154(b) by 1345 days.

(21) Appl. No.: 17/610,606

(22) PCT Filed: May 8, 2020

(86) PCT No.: PCT/CN2020/089217

§ 371 (c)(1),
(2) Date: Nov. 11, 2021

(87) PCT Pub. No.: WO2020/228610

PCT Pub. Date: Nov. 19, 2020

(65) Prior Publication Data

US 2022/0211857 A1 Jul. 7, 2022

(30) Foreign Application Priority Data

May 10, 2019 (CN) ......................... 201910390476.3

(51) Int. Cl.

| | |
|---|---|
| ***C12N 15/70*** | (2006.01) |
| ***A61K 38/00*** | (2006.01) |
| ***A61K 47/54*** | (2017.01) |
| ***A61K 47/64*** | (2017.01) |
| ***C07K 14/605*** | (2006.01) |

(52) U.S. Cl.

CPC ............ *A61K 47/64* (2017.08); *A61K 47/545* (2017.08)

(58) Field of Classification Search

CPC .... A61K 47/64; A61K 47/545; A61K 47/542; A61K 38/00; C07K 14/605; C07K 14/62; C07K 14/635; C12Y 601/01026; A61P 3/10

See application file for complete search history.

(56) References Cited

FOREIGN PATENT DOCUMENTS

| | | | | |
|---|---|---|---|---|
| CN | 101133082 A | 2/2008 | | |
| CN | 102504022 A | 6/2012 | | |
| CN | 104099360 A | 10/2014 | | |
| CN | 107073130 A | 8/2017 | | |
| CN | 107108710 A | 8/2017 | | |
| CN | 110545849 A | 12/2019 | | |
| JP | 2010535849 A | 11/2010 | | |
| WO | WO-2006097537 A2 * | 9/2006 | ................ | A61P 3/06 |
| WO | 2013/018929 A1 | 2/2013 | | |
| WO | 2018069481 A1 | 4/2018 | | |

OTHER PUBLICATIONS

CN102504022 English machine translation, pp. 1-24 (2012) (Year: 2012).*

Wan et al, "Pyrrolysyl-tRNA Synthetase: an ordinary enzyme but an outstanding genetic code expansion tool," Biochim Biophys Acta. 1844(6): 1059-1070 (2014) (Year: 2014).*

CN104099360 English machine translation, pp. 1-31 (Year: 2014).*

Zibo Fan et al., "Modification at Lys24 with fatty acid generates active calcitonin gene-related peptide with much improved plasma stability", Journal of Chinese Pharmaceutical Sciences, Sep. 29, 2018, Nolume. 27, No. 9, pp. 589-599, China.

Zhang Mei et al., "Research Advances of Fusion Protein of Parathyroid Hormone", Biotechnology Bulletin, No. 3, Mar. 26, 2009, pp. 25-28, China.

* cited by examiner

*Primary Examiner* — Julie Ha
*Assistant Examiner* — Kristina M Hellman
(74) *Attorney, Agent, or Firm* — NKL Law; Bin Lu; Allen Xue

(57) ABSTRACT

The present invention discloses a polypeptide derivative, its preparation method, and pharmaceutical uses thereof. The derivative comprises a polypeptide (insulin, glucagon-like peptide-1, or PTH) and a fatty acid acyl modifying group L, which is linked to the polypeptide's lysine residue via a click reaction to yield a series of derivatives. Experimental data demonstrate that these derivatives retain biological activity while exhibiting significantly extended in vivo half-lives, and they are useful for preparing medicaments to treat or prevent diseases such as diabetes.

6 Claims, No Drawings

Specification includes a Sequence Listing.

POLYPEPTIDE DERIVATIVE AND PREPARATION METHOD THEREOF

INCORPORATION OF SEQUENCE LISTING

This application contains a sequence listing in Computer Readable Form (CRF). The CFR file containing the sequence listing entitled "PBA4085119-SequenceListing.txt", which was created on Nov. 11, 2021, and is 7,555 bytes in size. The information in the sequence listing is incorporated herein by reference in entirety.

TECHNICAL FIELD

The present invention relates to the field of biomedicine, and in particular to a polypeptide derivative and a preparation method thereof.

BACKGROUND

Pharmacokinetic studies have shown that polypeptide/protein drugs are eliminated in vivo mainly through degradation, excretion, and receptor-mediated endocytosis, etc. Polypeptide factors with a molecular weight of less than 20 kilodalton (kDa) are easily filtered by glomerulus during metabolism, and when they pass through renal tubules, they are partially degraded by proteases and excreted in urine, so they have short half-lives. Take glucagon-like peptide-1 (GLP-1) for example, generally its biological half-life in vivo is 20 minutes. High-dose medication is required frequently to achieve therapeutic effect. Long-term and frequent injections not only increase suffering of patients and treatment costs, but also make it easy to cause a series of serious side effects. Development of long-acting polypeptide/protein drugs has become an important trend for secondary development of first generation of genetically engineered polypeptide/protein drugs. At present, prolonging half-life of protein drugs is mainly based on two aspects. On the one hand, increasing molecular weight of protein drugs to reduce glomerular filtration rate and immunogenicity of heterologous proteins, thereby reduce clearance rate in vivo thereof. On the other hand, releasing drugs continuously and slowly to maintain their concentration, thereby prolong action time thereof. Commonly used techniques comprise: preparation of sustained release agents, construction of mutants, chemical modification and gene fusion, etc.

Therefore, in the present invention, half-life of proteins or polypeptides in blood can be prolonged by fatty acid modification thereof and a non-covalent bond between the fatty acid and albumin.

SUMMARY OF THE INVENTION

The purpose of the present invention is to provide a new and longer-acting polypeptide derivative.

In the first aspect of the present invention, it provides a polypeptide derivative, which comprises:

(a) a polypeptide; and (b) a modified group L linked to a lysine site of the polypeptide as shown in Formula I, Formula I

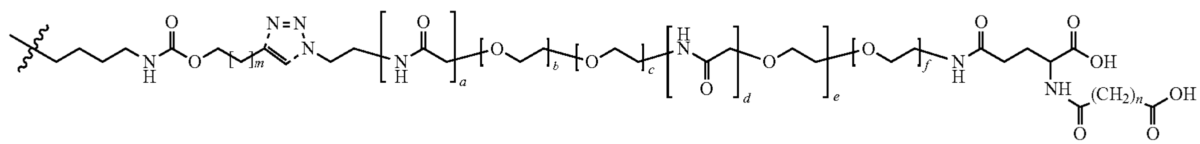

wherein a wavy line represents a link position with the lysine site, and m is an integer of 0-8; a, b, c, d, e and f are independent integers selected from 0 to 10; n is an integer from 14 to 16.

In another preferred embodiment, the group L is selected from the group consisting of:

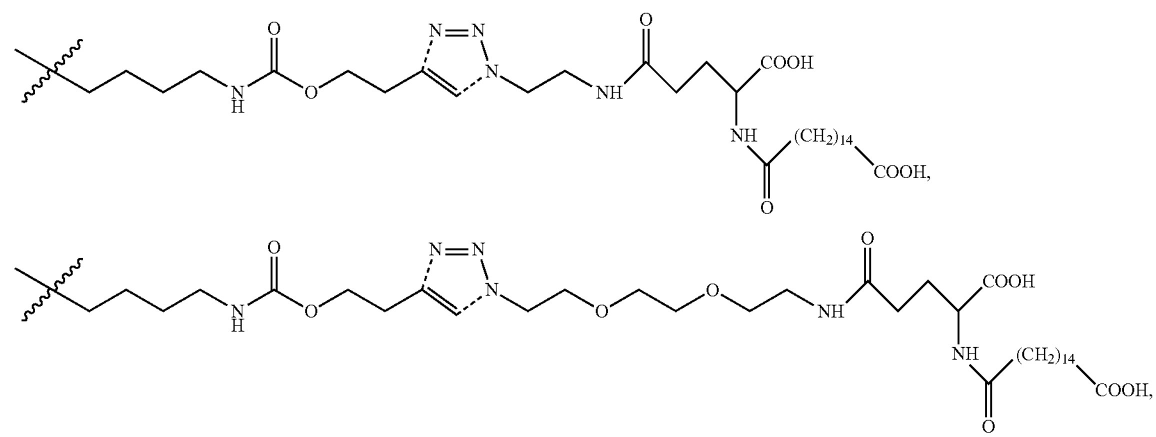

-continued

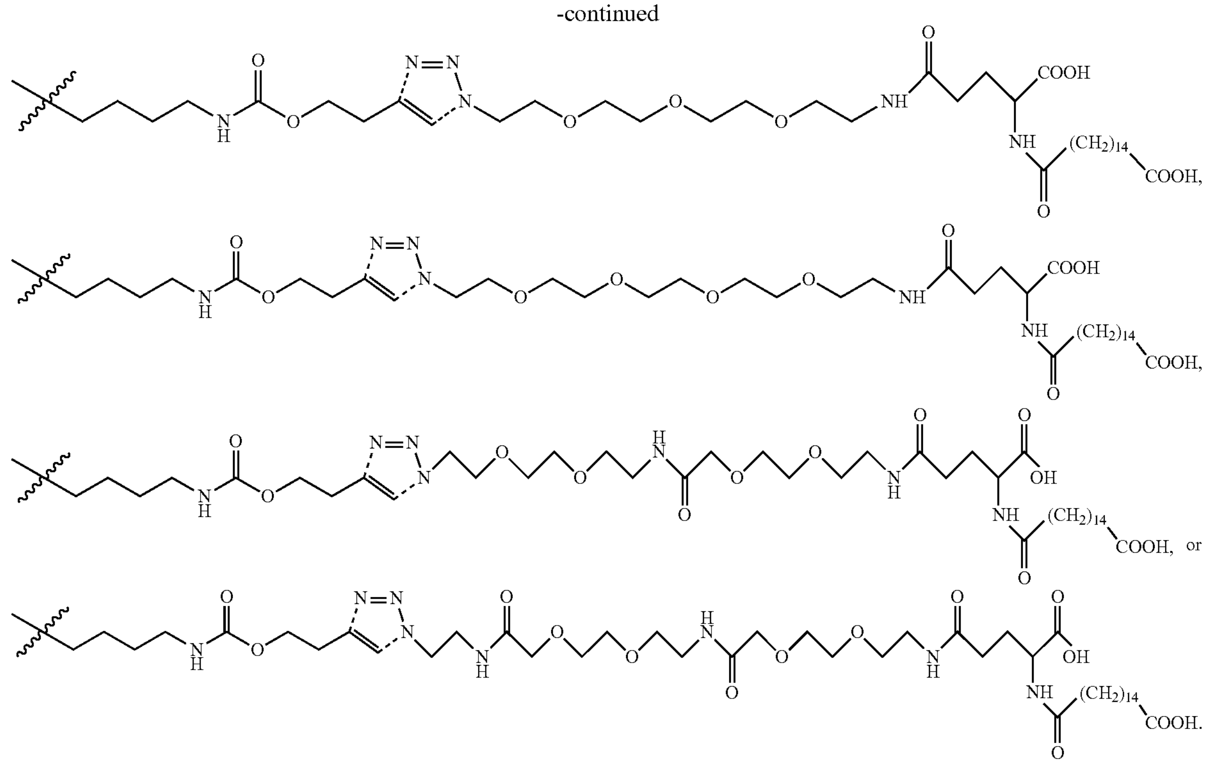

In another preferred embodiment, the polypeptide is selected from the group consisting of: an insulin, glucagon-like peptide-1 (GLP-1), parathyroid hormone (PTH), and combinations thereof.

In another preferred embodiment, the polypeptide derivative is selected from the group consisting of: an insulin derivative, a GLP-1 derivative, a PTH derivative, and combinations thereof.

In another preferred embodiment, an A chain of the insulin has a sequence as shown in SEQ ID NO: 1 or 2.

In another preferred embodiment, a B chain of the insulin has a sequence as shown in SEQ ID NO: 3, 4, 5 or 6.

In another preferred embodiment, the GLP-1 has a sequence as shown in any one of SEQ ID NO: 7-9.

In another preferred embodiment, the PTH has a sequence as shown in SEQ ID NO: 10.

In another preferred embodiment, a structure of the polypeptide derivative is shown below, wherein

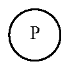

is an insulin, GLP-1 or PTH:

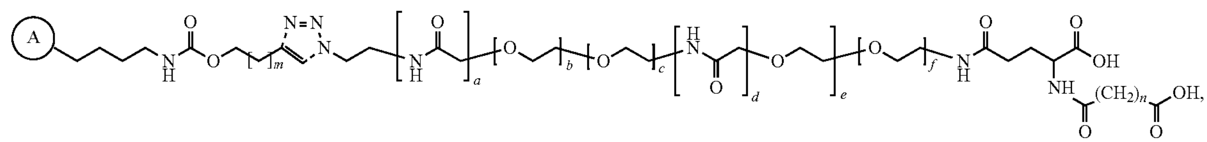

wherein m is an integer of 0-8; a, b, c, d, e and f are independent integers selected from 0 to 10; n is an integer from 14 to 16.

In another preferred embodiment, the polypeptide derivative is selected from the group consisting of:

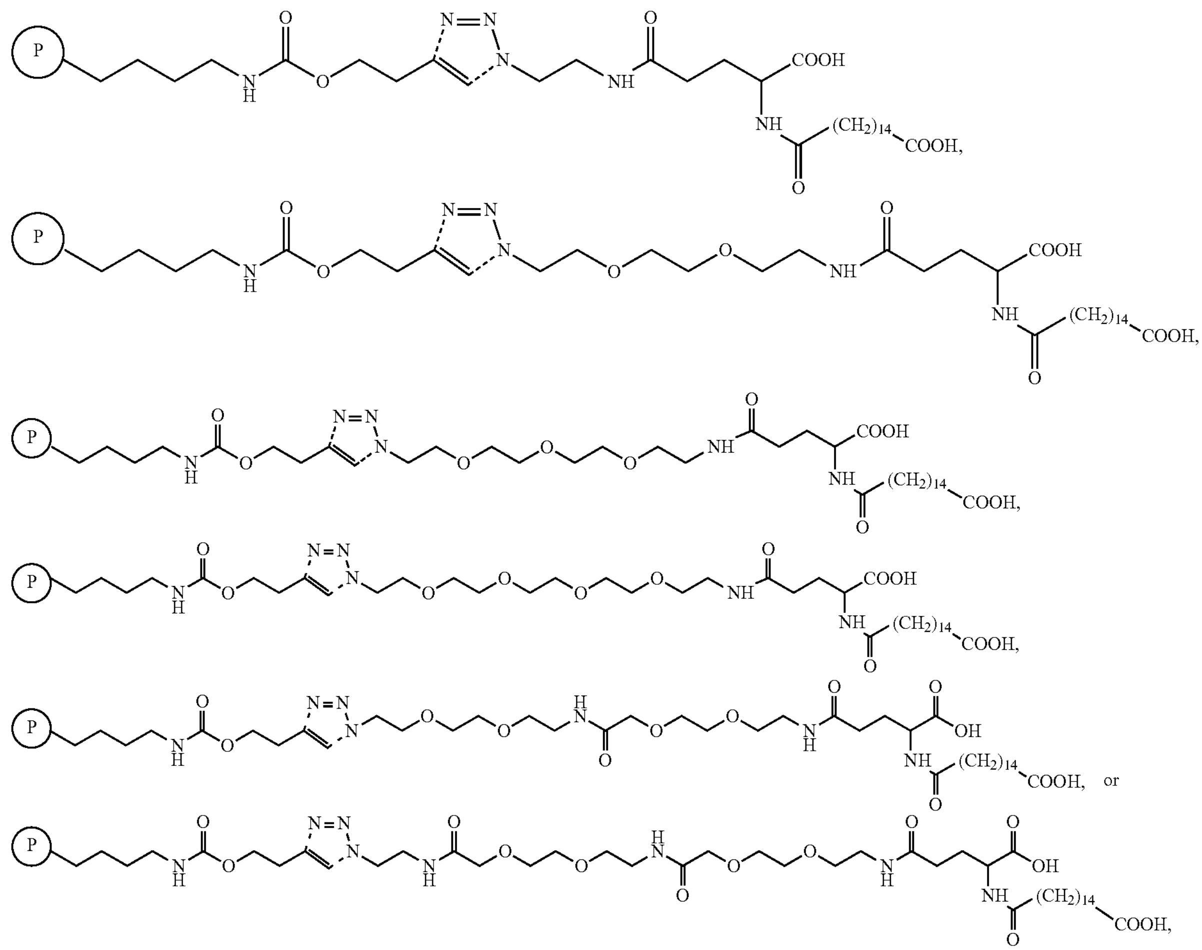

wherein

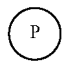

is an insulin, GLP-1 or PTH.

In another preferred embodiment, the polypeptide derivative is selected from the group consisting of: L0-GFA16-polypeptide, L2-GFA16-polypeptide, L3-GFA16-polypeptide, L4-GFA16-polypeptide, L5-GFA16-polypeptide, or L6-GFA16-polypeptide.

In another preferred embodiment, a structure of the L0-GFA16-polypeptide is shown below, wherein

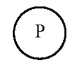

is a polypeptide:

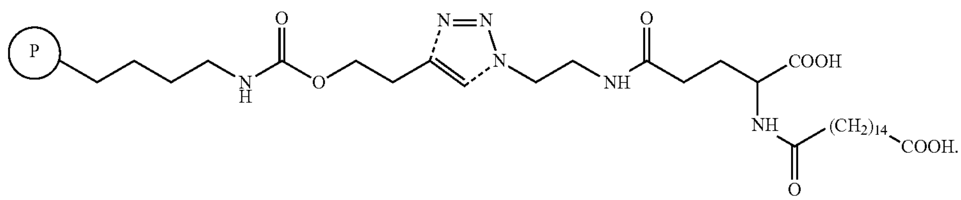

In another preferred embodiment, a structure of the L2-GFA16-polypeptide is shown below, wherein

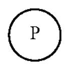

is a polypeptide:

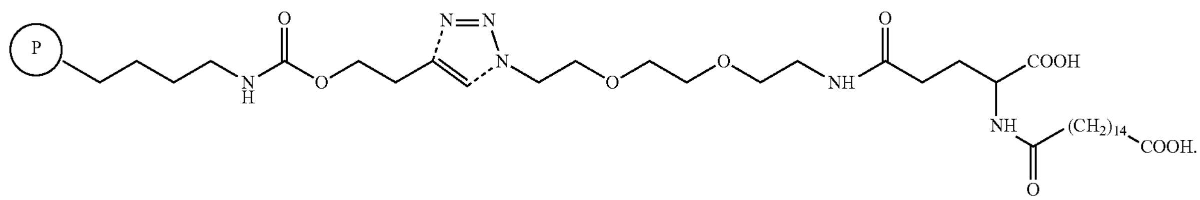

In another preferred embodiment, a structure of the L3-GFA16-polypeptide is shown below, wherein

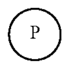

is a polypeptide:

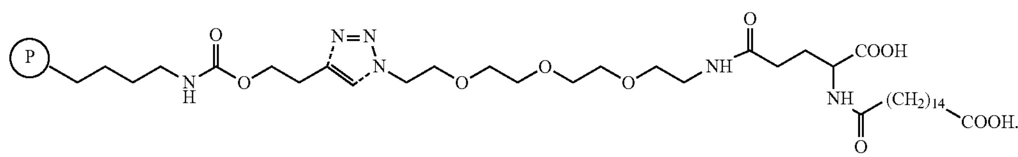

In another preferred embodiment, a structure of the L4-GFA16-polypeptide is shown below, wherein

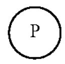

is a polypeptide:

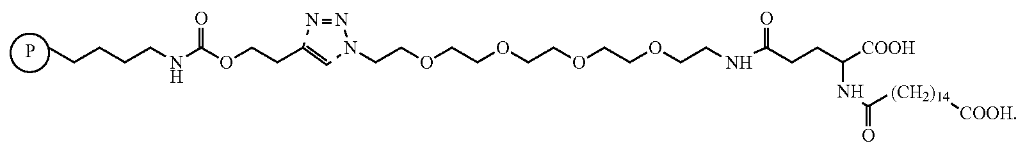

In another preferred embodiment, a structure of the L5-GFA16-polypeptide is shown below, wherein

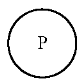

is a polypeptide:

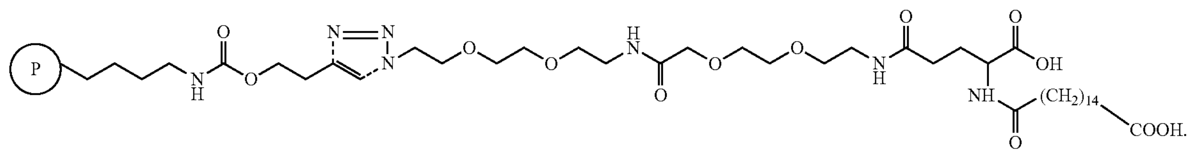

In another preferred embodiment, a structure of the L6-GFA16-polypeptide is shown below, wherein

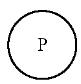

is a polypeptide:

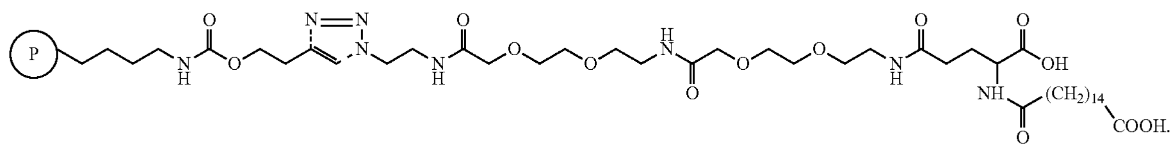

YTPKT (SEQ ID NO: 16) or YTKPT (SEQ ID NO: 17) motif, and the modified group L is linked to the lysine (K) site of the motif.

In another preferred embodiment, the modified group L is linked to the 28th or 29th lysine (K) of the B chain.

In another preferred embodiment, the modified group L is covalently linked to the 29th lysine (K) of the sequence as shown in SEQ ID NO: 3, 4, or 6.

In another preferred embodiment, the insulin comprises an A chain and a B chain.

In another preferred embodiment, the insulin comprises a human insulin or an animal insulin, and preferably a human insulin.

In another preferred embodiment, the animal insulin comprises a porcine insulin and a bovine insulin.

In another preferred embodiment, the A chain and B chain of the insulin further comprise one or more disulfide bonds.

In another preferred embodiment, the insulin comprises a natural insulin, an insulin precursor, or a variant of insulin.

In another preferred embodiment, the insulin derivative comprises an insulin precursor and the modified group L.

In another preferred embodiment, the A chain of the insulin has the sequence as shown in SEQ ID NO: 1 or 2.

In another preferred embodiment, the B chain of the insulin has the sequence as shown in SEQ ID NO: 3, 4, 5 or 6.

In another preferred embodiment, the A chain of the insulin has the sequence as shown in SEQ ID NO: 1, and the B chain of the insulin has the sequence as shown in SEQ ID NO: 3, 5 or 6.

In another preferred embodiment, the A chain of the insulin has the sequence as shown in SEQ ID NO: 2, and the B chain of the insulin has the sequence as shown in SEQ ID NO: 4 or 6.

In another preferred embodiment, the modified group Lis covalently linked to the lysine (K) site.

In another preferred embodiment, the modified group L is covalently linked to a ε-amino group of the lysine (K).

In another preferred embodiment, the insulin comprises a PK, DKT, PKT or KPT motif, and the modified group L is linked to the lysine (K) site of the motif.

In another preferred embodiment, the insulin comprises a TPK, TKP or TDK motif, and the modified group L is linked to the lysine (K) site of the motif.

In another preferred embodiment, the insulin comprises a YTPK (SEQ ID NO: 14), YTDKT (SEQ ID NO: 15), In another preferred embodiment, the B chain of the insulin has a sequence as shown in SEQ ID NO: 3, 4 or 6, and the modified group L is linked to the 29th lysine (K) of the sequence as shown in SEQ ID NO: 3, 4, or 6.

In another preferred embodiment, the B chain of the insulin has a sequence as shown in SEQ ID NO: 5, and the modified group L is linked to the 28th lysine (K) of the sequence as shown in SEQ ID NO: 5.

In another preferred embodiment, the insulin derivative is selected from the group consisting of: L0-GFA16-insulin, L2-GFA16-insulin, L3-GFA16-insulin, L4-GFA16-insulin, L5-GFA16-insulin, or L6-GFA16-insulin.

In another preferred embodiment, the GLP-1 derivative comprises a GLP-1 analog and the modified group L.

In another preferred embodiment, the GLP-1 has the sequence as shown in any one of SEQ ID NO: 7-9.

In another preferred embodiment, the modified group Lis covalently linked to the lysine (K) site.

In another preferred embodiment, the modified group L is covalently linked to a &-amino group of the lysine (K).

In another preferred embodiment, the GLP-1 comprises an AKE motif, and the modified group L is linked to the lysine (K) site of the motif.

In another preferred embodiment, the GLP-1 comprises an AAKEF (SEQ ID NO: 18) motif, and the modified group L is linked to the lysine (K) site of the motif.

In another preferred embodiment, the modified group L is linked to the 20th or 26th lysine (K) of the chain.

In another preferred embodiment, the GLP-1 derivative is selected from the group consisting of: L0-GFA16-GLP-1, L2-GFA16-GLP-1, L3-GFA16-GLP-1, L4-GFA16-GLP-1, L5-GFA16-GLP-1, or L6-GFA16-GLP-1.

In another preferred embodiment, the PTH derivative comprises a PTH analog and the modified group L.

In another preferred embodiment, the PTH has the sequence as shown in SEQ ID NO: 10.

In another preferred embodiment, the modified group Lis covalently linked to the lysine (K) site.

In another preferred embodiment, the modified group L is covalently linked to a ε-amino group of the lysine (K).

In another preferred embodiment, the PTH comprises an RKR motif, and the modified group L is linked to the lysine (K) site of the motif.

In another preferred embodiment, the PTH comprises the LRKRL (SEQ ID NO: 19) motif, and the modified group L is linked to the lysine (K) site of the motif.

In another preferred embodiment, the modified group L is linked to the 26th lysine (K) of the PTH.

In another preferred embodiment, the PTH derivative is selected from the group consisting of: L0-GFA16-PTH, L2-GFA16-PTH, L3-GFA16-PTH, L4-GFA16-PTH, L5-GFA16-PTH, or L6-GFA16-PTH.

In the second aspect of the present invention, it provides a pharmaceutical composition which comprises the polypeptide derivative according to the first aspect of the present invention, and a pharmaceutically acceptable carrier.

In the third aspect of the present invention, it provides use of the polypeptide derivative according to the first aspect of the present invention for preparing drugs or preparations for preventing and/or treating osteoporosis, diabetes, hyperglycemia and other diseases which benefit from reducing blood glucose.

ciated tRNA thereof, wherein a lysine coding sequence of the polypeptide in the coding sequence is replaced with TAG (encoding a lysine derivative), thereby producing a compound of Formula IV; and

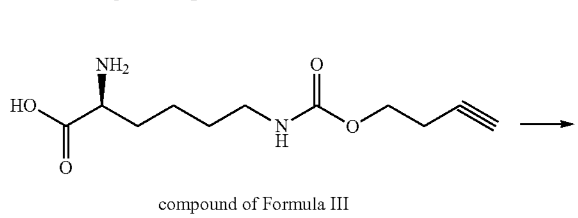

compound of Formula III

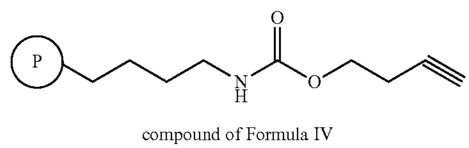

compound of Formula IV (2) undertaking a reaction between the compound of Formula IV and a compound of Formula V in an inert solvent, thereby producing the polypeptide derivative, compound of Formula V

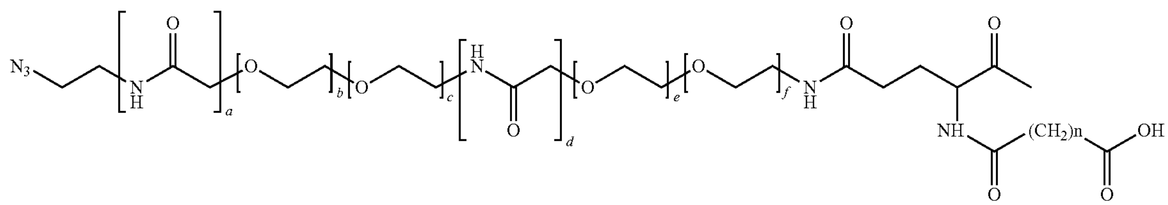

In the fourth aspect of the present invention, it provides a method for preparing a polypeptide derivative, which comprises the following steps:

(1) cultivating a strain containing an insulin coding sequence in the presence of a group X-lysine, a pyrrolysyl-tRNA synthetase and a homologous associated tRNA thereof, wherein a lysine coding sequence of the polypeptide in the coding sequence is replaced with TAG (encoding a lysine derivative), thereby producing the polypeptide derivative which comprises:

(a) a polypeptide chain; and (b) a modified group L linked to a lysine site of the polypeptide, and the modified group L is the group X as defined in the first aspect of the present invention; and optionally (2) separating the polypeptide derivative from fermentation products.

In another preferred embodiment, the polypeptide is selected from the group consisting of: an insulin, GLP-1, PTH, and combinations thereof.

In another preferred embodiment, the polypeptide derivative is selected from the group consisting of: an insulin derivative, a GLP-1 derivative, a PTH derivative, and combinations thereof.

In the fifth aspect of the present invention, it provides a method for preparing a polypeptide derivative, which comprises the following steps:

(1) cultivating a strain containing a polypeptide coding sequence in the presence of a compound of Formula III, a pyrrolysyl-tRNA synthetase and a homologous assowherein a, b, c, d, e and f are independent integers selected from 0 to 10; n is an integer from 14 to 16 in Formula V.

In another preferred embodiment, the polypeptide is selected from the group consisting of: an insulin, GLP-1, PTH, or combinations thereof.

In another preferred embodiment, the polypeptide derivative is selected from the group consisting of: an insulin derivative, a GLP-1 derivative, a PTH derivative, or combinations thereof.

In the sixth aspect of the present invention, it provides a method for preparing a polypeptide derivative, which comprises the following steps:

(1) cultivating a strain containing a polypeptide coding sequence in the presence of a compound of Formula VI, a pyrrolysyl-tRNA synthetase and a homologous associated tRNA thereof, wherein a lysine coding sequence of the polypeptide in the coding sequence is replaced with TAG (encoding a lysine derivative), thereby producing a compound of Formula VII; and

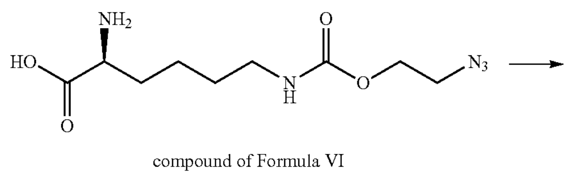

compound of Formula VI

-continued

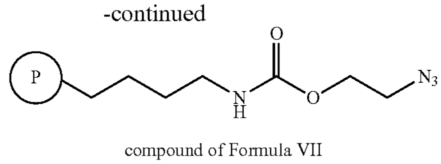

compound of Formula VII (2) undertaking a reaction between the compound of Formula VII and a compound of Formula VIII in an inert solvent, thereby producing the polypeptide derivative, compound of Formula VIII

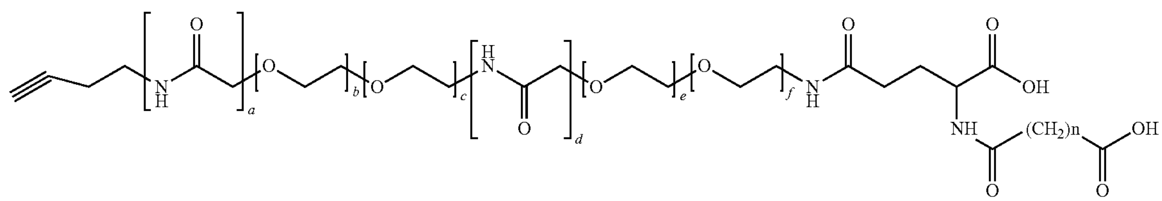

wherein a, b, c, d, e and f are independent integers selected from 0 to 10; n is an integer from 14 to 16 in Formula VIII.

In another preferred embodiment, the polypeptide is selected from the group consisting of: an insulin, GLP-1, PTH, or combinations thereof.

In another preferred embodiment, the polypeptide derivative is selected from the group consisting of: an insulin derivative, a GLP-1 derivative, a PTH derivative, or combinations thereof.

In the seventh aspect of the present invention, it provides an intermediate, which comprises:

(a) a polypeptide, wherein the polypeptide is an insulin, GLP-1, or PTH; and (b) a modified group L linked to a lysine site of the polypeptide, and the modified group L is a group as shown in Formula A, Formula A

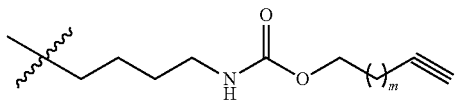

wherein a wavy line represents a link position with the lysine site, and m is an integer of 0-8.

In another preferred embodiment, a structure of the intermediate is shown in Formula IV, wherein

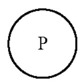

is an insulin, GLP-1 or PTH.

compound of Formula IV

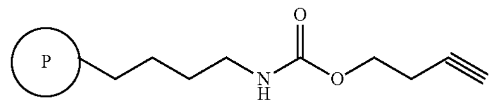

In another preferred embodiment, the intermediate is used for preparing the polypeptide derivative according to the first aspect of the present invention.

The present invention further provides use of the intermediate according to the seventh aspect of the present invention, wherein the intermediate is used for preparing the polypeptide derivative according to the first aspect of the present invention.

It should be understood that within the scope of the present invention, the above-mentioned technical features of the present invention and the technical features specifically described in the following (such as the embodiments) can be combined with each other to form a new or preferred technical solution, which are not redundantly repeated one by one due to space limitation.

DETAILED DESCRIPTION

After extensive and intensive research, the inventors have unexpectedly obtained a polypeptide derivative. Experimental results show that the polypeptide derivative has a significantly prolonged half-life while maintaining biological activity. The present invention further provides a pharmaceutical use of the polypeptide derivative and its functions of treating or preventing diabetes, promoting the osteogenesis of bone cells, and the like. On this basis, the inventors have completed the present invention.

Ideal effects of long-acting insulins are achieved by rebuilding basic insulin secretion in diabetic patients via insulin injections as few as possible. Chemical modification is one of the ways of obtaining long-acting insulins. Structure of chemical modifiers must be stable, non-toxic, and non-antigenic and have a suitable molecular weight. Specific chemical modification of the present invention can prolong half-life of insulins and reduce their antigenicity while maintaining biological activity thereof. A modified insulin derivative of the present invention is a polymer compound with good biocompatibility which is non-toxic to human bodies, and water solubility of drugs has increased. It can also reduce its clearance rate in glomerular and increase half-life of drugs when circulating in vivo, thereby obtain a long-term effect. Insulins, GLP-1, and PTH proteins containing a butynyloxycarbonyl-lysine of the present invention are linked to fatty acid acyl compounds by a click reaction to obtain a series of GLP-1 derivatives and PTH derivatives which have significantly prolonged half-lives.

Terms

Before illustrating the present invention, it should be understood that the present invention is not limited to the specific methods and experimental conditions as described herein due to variability of the methods and conditions. It should also be understood that the terms used herein are only to illustrate specific embodiments, not to limit the scope of the present invention which is only limited by appended claims.

As used herein, the term "about" may refer to a value varies from the recited value by no more than 1% when used for referring to a specifically recited value. For example, as used herein, the expression "about 100" includes all values between 99 and 101 (such as 99.1, 99.2, 99.3, 99.4, etc.).

As used herein, the terms "contain" or "comprise (or include)" can be open, semi-closed, and closed. In other words, the terms also include "substantially consisting of" or "consisting of".

GLP-1

GLP-1 is a glucose-dependent incretin polypeptide hormone which stimulates insulin secretion to avoid hypoglycemia. The characteristic of promoting insulin secretion which is glucose-dependent avoids risks of hypoglycemia that often exist in treatments of diabetes. With these physiological functions, the development of GLP-1 has broad prospects in being a treatment drug of type 2 diabetes thereof. GLP-1 usually functions on a GLP-1 receptor (i.e., GLP-1R) which is on a membrane of pancreatic islet B cells for promoting the secretion of insulin. However, although natural GLP-1 has many advantages in the treatment of diabetes, it is rapidly degraded in vivo by dipeptidyl peptidase-IV (i.e., DPP-IV), and it is rapidly filtered and metabolized by kidney. Thus, we need to modify the natural GLP-1 to screen out GLP-1 analogues which can resist DPP-IV degradation and can avoid rapid filtration and metabolism by kidney.

GLP-1 has functions of glucose-dependent incretin secretion; preventing a degeneration of pancreatic β cells and stimulating β cells to proliferate and differentiate; inducing a transcription of pre-insulin genes and promoting pre-insulin biosynthesis; increasing insulin sensitivity; increase a secretion of somatostatin and inhibiting a production of insulin and glucagon (which is also glucose-dependent).

Parathyroid Hormone (PTH)

Parathyroid hormone (PTH) is a single-chain polypeptide protein containing 84 amino acids, which is secreted by parathyroid gland. It is one of the most important peptide hormones that regulate a metabolism of calcium and phosphorus and bone turnover. Main physiological functions of hPTH (i.e., human PTH) are promoting an osteogenesis of bone cells, stimulating a reabsorption of calcium and a secretion of phosphorus in kidney, and bone reconstruction. A main disadvantage of PTH is that hPTH molecule does not comprise cysteine and is very unstable in vivo. PTHI has a small molecular weight and is easily filtered by glomerulus, so its half-life in vivo is short. The half-life of subcutaneous administration or intramuscular injection is generally about 12 hours. In order to achieve therapeutic effects, it is generally necessary to take high-dose medications frequently (i.e., subcutaneous injection once a day for several months). However, a frequent drug administration and a long treatment period make it difficult to bear for patients, and can cause headaches, vomiting, fever and other adverse reactions clinically, thereby causing poor patient compliance. Therefore, there is an urgent need for long-acting preparations of PTH or the like, which can be modified by parathyroid hormones to extend their half-lives.

Fatty Acid Acyl Compounds

Polypeptides (such as insulins, GLP-1, and PTH) containing a butynyloxycarbonyl-lysine of the present invention are linked to fatty acid acyl compounds by a click reaction to obtain a series of polypeptide derivatives which have significantly prolonged half-lives.

A fatty acid acyl compound of the present invention comprises 14-18 carbons, and its structure is shown in the following Formula V or Formula VIII:

Formula V

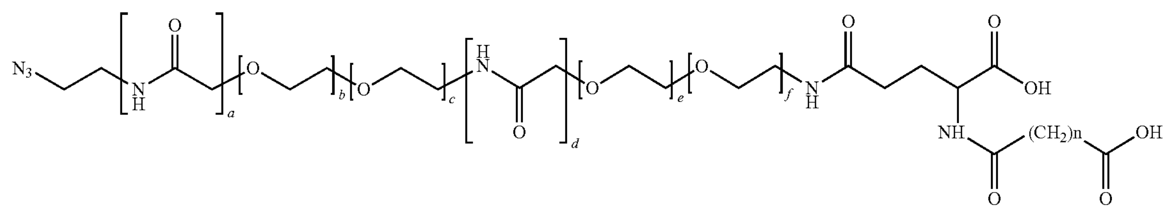

Formula VIII

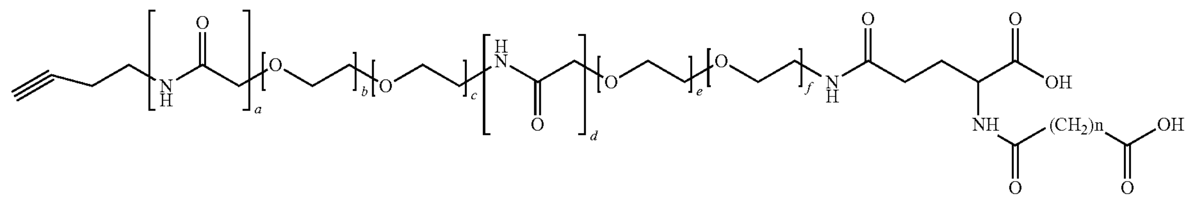

wherein a, b, c, d, e and f are independent integers selected from 0 to 10; n is an integer from 14 to 16.

In another preferred embodiment, the fatty acid acyl compound is selected from the group consisting of: L0-GFA, L2-GFA, L3-GFA, L4-GFA, L5-GFA, or L6-GFA.

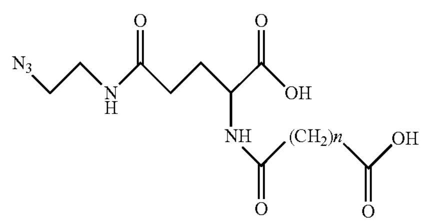
L0-GFA
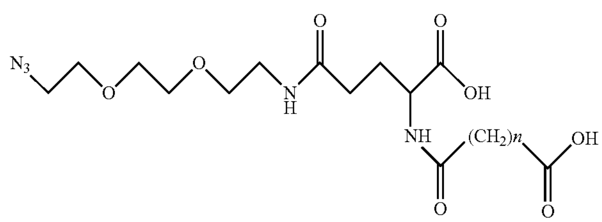
L2-GFA
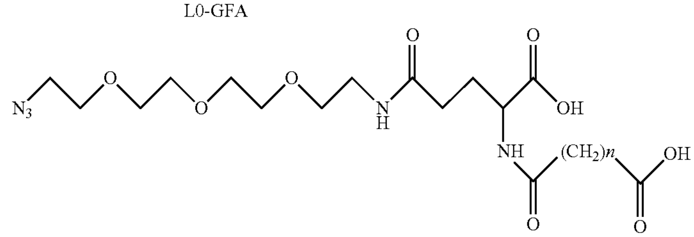
L3-GFA
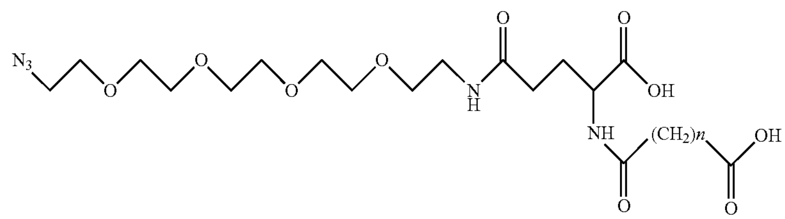
L4-GFA
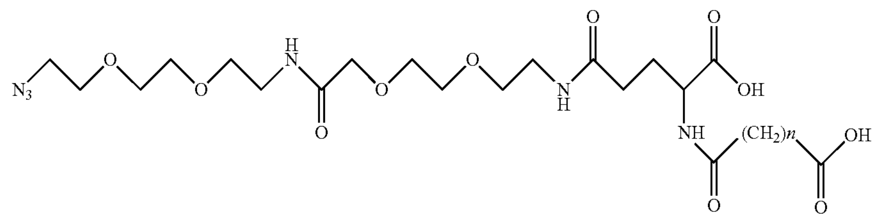
L5-GFA
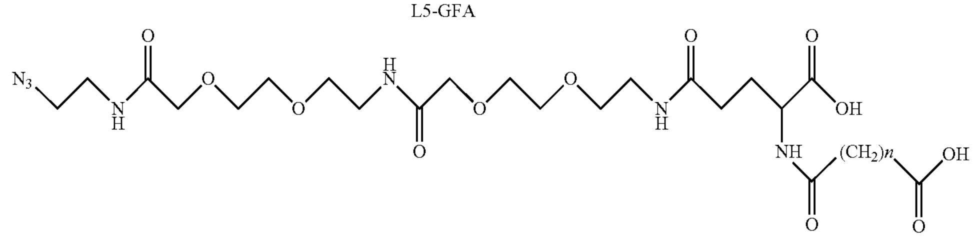
L6-GFA
In another preferred embodiment, the fatty acid acyl compound is selected from the group consisting of: L0-GFA16, L2-GFA16, L3-GFA16, L4-GFA16, L5-GFA16, or L6-GFA16.
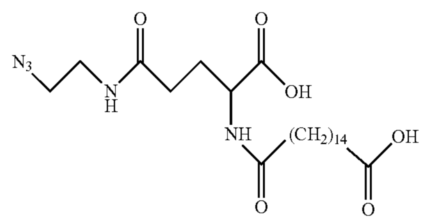
L0-GFA16
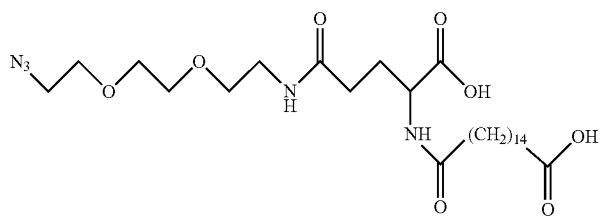
L2-GFA16

-continued

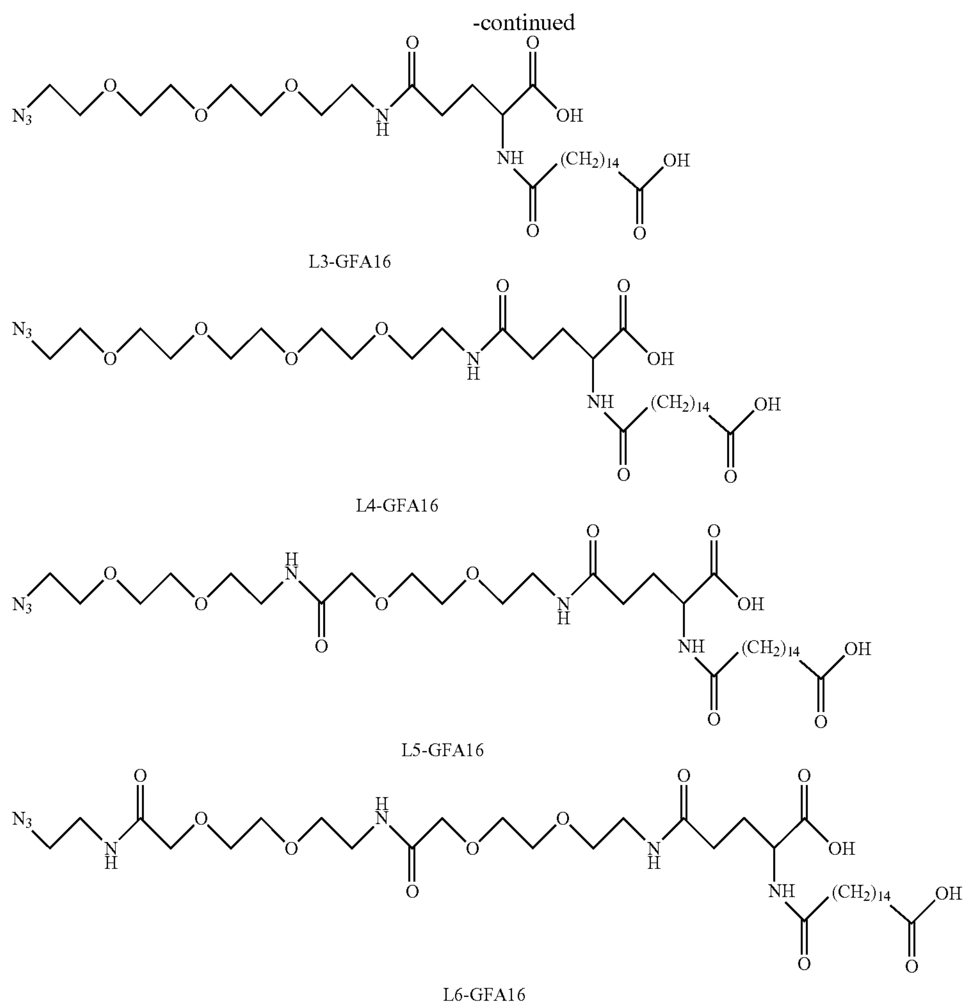

L3-GFA16

L4-GFA16

L5-GFA16

L6-GFA16

Polypeptide Derivatives

As used herein, terms “a polypeptide analog”, “a polypeptide derivative” and “a derivative of the present invention” are used interchangeably and all refer to the polypeptide derivative according to the first aspect of the present invention.

In the present invention, it further provides a polypeptide derivative according to the first aspect of the present invention.

Specifically, the polypeptide derivative comprise:

(a) a polypeptide chain; and (b) a modified group L linked to a lysine site of the polypeptide, and the modified group L is the group X as shown in Formula I, wherein a wavy line represents a link position with the lysine site, and m is an integer of 0-8; a, b, c, d, e and f are independent integers selected from 0 to 10; n is an integer from 14 to 16.

In another preferred embodiment, the polypeptide derivative comprises an insulin derivative, a GLP-1 derivative, a PTH derivative, and combinations thereof.

In another preferred embodiment, an A chain of the insulin has a sequence as shown in SEQ ID NO: 1 or 2.

In another preferred embodiment, a B chain of the insulin has a sequence as shown in SEQ ID NO: 3, 4, 5 or 6.

Formula I

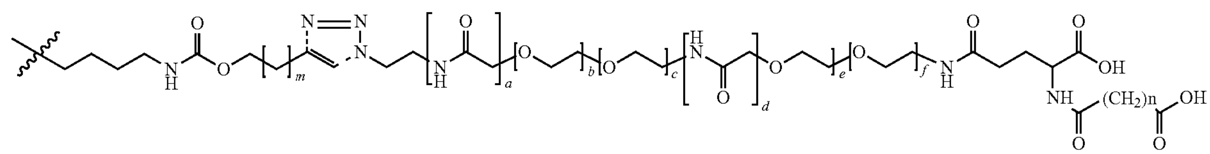

(SEQ ID NO: 1)
GIVEQCCTSICSLYQLENYCN (SEQ ID NO: 2)
GIVEQCCTSICSLYQLENYCG (SEQ ID NO: 3)
FVNQHLCGSHLVEALYLVCGERGFFYTPKT (SEQ ID NO: 4)
FVNQHLCGSHLVEALYLVCGERGFFYTPK (SEQ ID NO: 5)
FVNQHLCGSHLVEALYLVCGERGFFYTKPT (SEQ ID NO: 6)
FVNQHLCGSHLVEALYLVCGERGFFYTDKT

In another preferred embodiment, the GLP-1 has the sequence as shown in any one of SEQ ID NO: 7-9.

(SEQ ID NO: 7)
HAEGTFTSDVSSYLEGQAAKEFIAWLVKGRG (SEQ ID NO: 8)
HAEGTFTSDVSSYLEGQAAKEFIAWLVRGRG (SEQ ID NO: 9)
HXEGTFTSDVSSYLEGQAAKEFIAWLVRGRG
(wherein X is 2-aminoisobutyric acid (Aib))

In another preferred embodiment, the PTH has the sequence as shown in SEQ ID NO: 10.

(SEQ ID NO.: 10)
SVSEIQLMHNLGRHLNSMERVEWLRKRLQDVHNF

In the present invention, an insulin derivative comprises an insulin, an insulin precursor and a variant of insulin. The variant of insulin is different from any naturally-occurring insulin, but can still perform a function which is similar to a human insulin by blood glucose control in the human body. Through genetic engineering of an underlying DNA, an amino acid sequence of the insulin can be changed, thereby changing its absorption, distribution, metabolism and secretion properties. Improvements comprise insulin analogues which are more easily absorbed by an injection site, thus they function faster than subcutaneously injected natural insulins. They are intended to supply a drug level of insulins (i.e., prandial insulin) required for mealtimes, while those insulin analogs released slowly between 8 hours and 24 hours are intended to provide a basal level of insulins (i.e., basal insulin) during the day, especially at night. Quick-acting insulin analogues comprise insulin lispro (Eli Lilly and Company) and insulin aspart (Novo Nordisk Company), while long-acting insulin analogues comprise NPH insulin, insulin glulisine (Sanofi Aventis Company), insulin detemir (Novo Nordisk Company) and insulin glargine (Sanofi Aventis Company).

As used herein, the term "variant" comprise any variant in which (a) one or more amino acid residues are replaced by a natural or unnatural amino acid residue; (b) the order of two or more amino acid residues is reversed; (c) (a) and (b) exist simultaneously; (d) a spacer group is between any two amino acid residues; (e) one or more amino acid residues are in peptoid form; (f) (NCC) main chain in one or more amino acid residues of the peptide is modified, or any combination of (a) to (f). Preferably, the variant is one of (a), (b) or (c).

More preferably, one or two amino acid residues are replaced by one or more other amino acid residues. And more preferably, one amino acid residue is replaced by another amino acid residue. Preferably, the substitution is homologous.

Homologous substitutions may occur (terms "substitution" and "replacement" used herein refer to the exchange of existing amino acid residues with optional residues), that is, homogeneous substitutions, such as substitutions between basic residues and basic residues, substitutions between acidic residues and acidic residues, substitutions between polar residues and polar residues, etc. Non-homologous substitutions may also occur, that is, one kind of residue is replaced by another kind, or substitutions alternatively comprise unnatural amino acids such as ornithine, 2-aminobutyric acid-ornithine, norleucine-ornithine, pyridyl-kanamycin and 17 μg/mL chloramphenicol, and cultured at 37° C. until $OD_{600}$ reached 2-4. 25% arabinose solution was added to the medium at a final concentration of 0.25%, and 0.1 M butynyloxycarbonyl-lysine solution was added at a final concentration of 5 mM to induce the expression of a fusion protein. The culture solution was cultured for 16-20 hours, and then collected by centrifugation (10000 rpm, 5 min, 4° C.).

The amino acid sequence of SEQ ID NO: 11:
MVSKGEELFTGVTYKTRA-
EVKFEGDDDDDKTLVNRIELKGIDFENLYFQGRFV
NQHLCGSHLVEALYLVCGERGFFYTPKTR-
GIVEQCCTSICSLYQLENYCN, wherein the 80th K was a lysine to which a butynyloxycarbonyl group was covalently attached.

The fusion proteins were expressed in the form of insoluble "inclusion bodies". In order to release the inclusion bodies, the *E. coli* cells were disrupted with a high-pressure homogenizer. Cell debris and soluble *E. coli* host proteins were removed by centrifugation at 5000 g. The inclusion bodies were washed with a solution containing TWEEN80 (polysorbate 80), ethylenediaminetetraacetic acid (EDTA), and NaCl, and then washed with pure water 1-2 times. The washed inclusion bodies were dissolved in 7.5M urea, which contained 2-10 mM β-mercaptoethanol with a pH of 10.5-11.5, so that the concentration of a total protein after a dissolution reached 10-25 mg/mL. The sample was diluted 5-10 times, maintained between 4-8° C., and routinely folded for 14-30 hours under the pH condition of 10.5-11.7. An enzyme digestion was performed with trypsin and carboxypeptidase B for 10-20 hours at 18-25° C., and the pH value was maintained between 8.0-9.5. Then 0.45M ammonium sulfate was added to terminate the enzyme digestion. Reversed-phase high-performance liquid chromatography (HPLC) analysis results showed that a yield of the enzyme digestion step was higher than 90%. An insulin analog obtained after the enzyme digestion with trypsin and carboxypeptidase B was named butynyloxycarbonyl-lysine-human insulin. The sample was clarified by membrane filtration. After initial purification by hydrophobic chromatography with 0.45M ammonium sulfate as buffer A and pure water as buffer B, a crude extract of butynyloxycarbonyl-lysine-human insulin was obtained with a purity of 90% confirmed by electrophoresis. After a purification by reverse-phase polymer packings and reverse-phase C8 packings, butynyloxycarbonyl-lysine-human insulin with a purity higher than 99% was finally obtained.

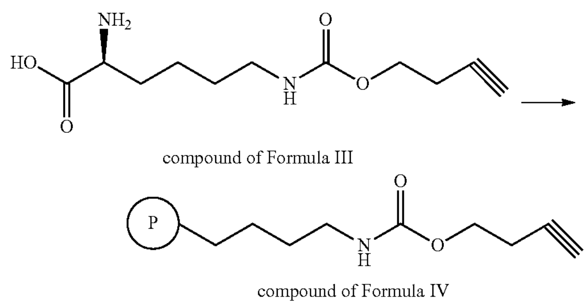

compound of Formula III compound of Formula IV

Example 2 Synthesis of L0-GFA16-Insulins (n is 14)

Since a fatty acid acyl compound had an azide group, an insulin protein with a terminal alkyne was introduced using the principle of "click chemistry", and the alkyne reacted with the azide to generate a 1,2,3-triazole ring, forming a cross-link. 4 μL of copper sulfate (50 μM) was added to a clean 1.5 mL centrifuge tube, then 3 μL of Bis (tri-tert-butylphosphine) tetrafluoroborate (BTTAA) (300 μM) was added and 10 μL of a compound IV (N-(butynyloxycarbonyl)-lysine-human insulin protein) (approximately 5 μM) which was prepared in Example 1 was added in order. At this time, the solution could be diluted to an appropriate volume or protein concentration. To this solution, 1 μL of L0-GFA16 (1 mM) was added, and 2 μL of sodium ascorbate (2.5 mM) was added to initiate the reaction. After about 1 hour at room temperature, 5 μL of sodium dodecyl sulfate-polyacrylamide gel electrophoresis (SDS-PAGE) sample buffer was added and heated to 100° C. for 10 minutes. An analysis of the solution was completed by 12% SDS-PAGE. A gel was recovered, then analyzed by gel imaging and fluorescence analysis, and then stained with Coomassie brilliant blue.

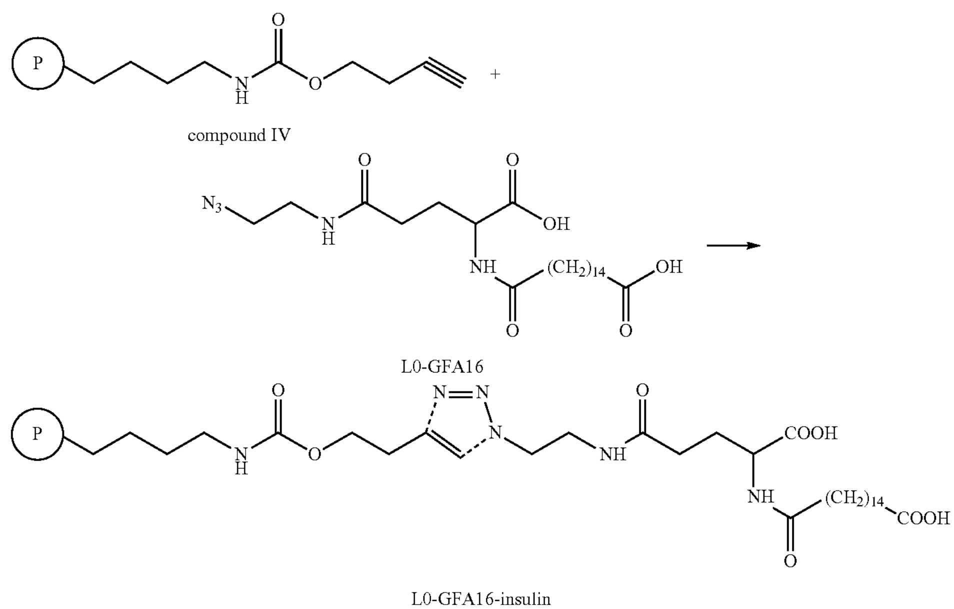

compound IV

L0-GFA16

L0-GFA16-insulin

Example 3 Synthesis of L2-GFA16-Insulins, L3-GFA16-Insulins, L4-GFA16-Insulins, L5-GFA16-Insulins and L6-GFA16-Insulins (n is 14)

4 μL of copper sulfate (50 μM) was added to a clean 1.5 mL centrifuge tube, then 3 μL of BTTAA (300 μM) was added and 10 μL of a compound IV (N-(butynyloxycarbonyl)-lysine-human insulin protein) (approximately 5 μM) which was prepared in Example 1 was added in order. At this time, it may be necessary to add water to dilute the solution to a proper volume or protein concentration. To this solution, 1 μL of L2-GFA16 (1 mM) was added, and 2 μL of sodium ascorbate (2.5 mM) was added to initiate the reaction. After about 1 hour at room temperature, 5 μL of SDS-PAGE sample buffer was added and heated to 100° C. for 10 minutes. An analysis of the solution was completed by 12% SDS-PAGE. A gel was recovered, then analyzed by gel imaging and fluorescence analysis, and then stained with Coomassie brilliant blue.

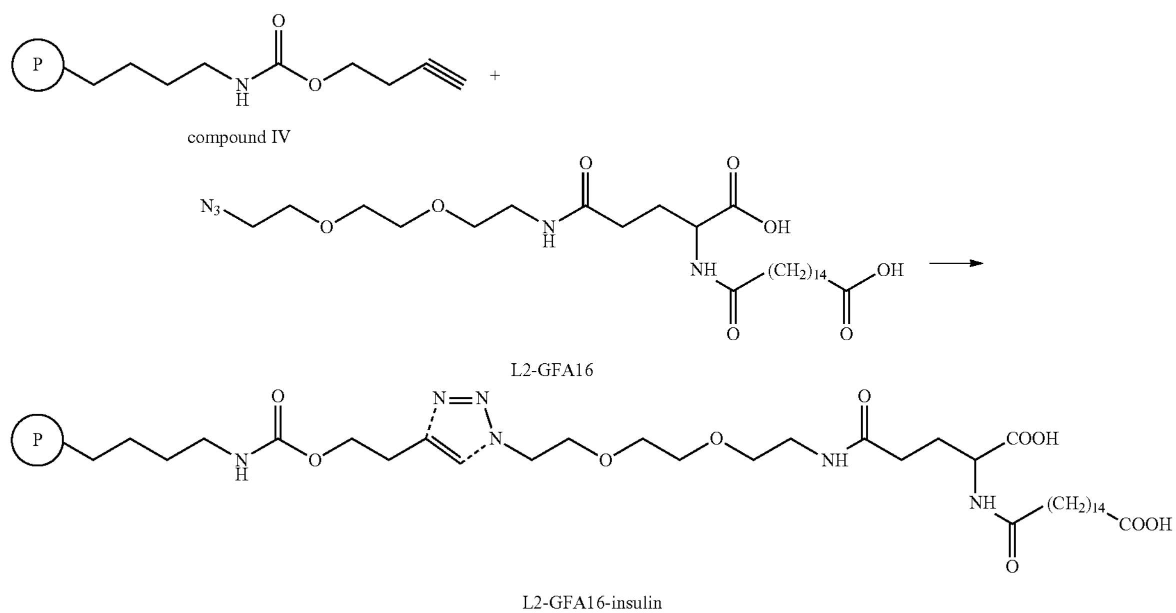
compound IV
L2-GFA16
L2-GFA16-insulin
Similarly, the compound IV prepared in Example 1 and L3-GFA16, L4-GFA16, L5-GFA16, and L6-GFA16 were respectively used to complete a click reaction to obtain the following products, and their structures were shown below.
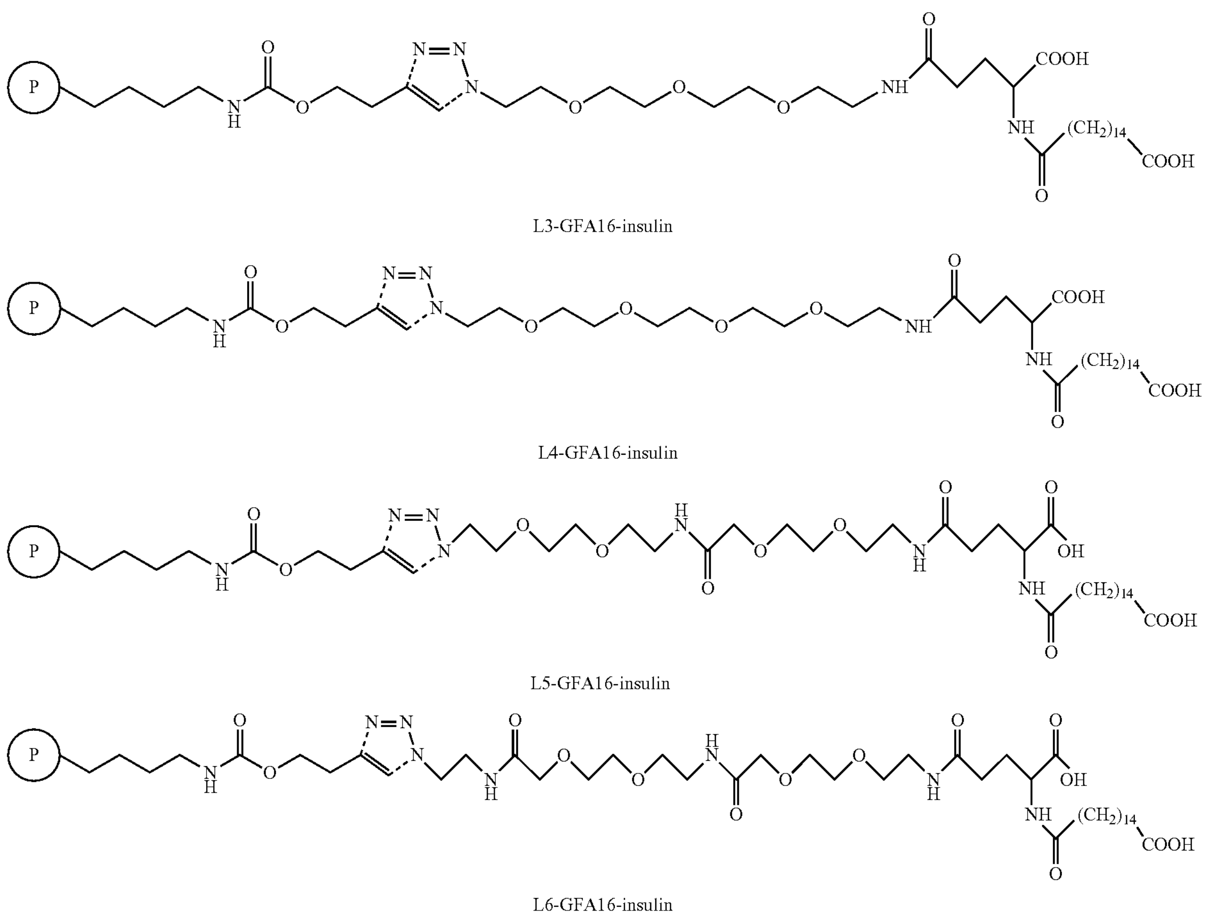
L3-GFA16-insulin
L4-GFA16-insulin
L5-GFA16-insulin
L6-GFA16-insulin Example 4 Pharmacokinetics Studies of Insulin Derivatives of the Present Invention in Rats The experiment comprised a reference substance group and a test substance group. Recombinant human insulins and L6-GFA16-insulins were injected subcutaneously with a single administration of 0.45 mg/kg, respectively. Animals in each group were collected blood at 15 min, 30 min, 1 h, 2 h, 3 h, 5 h, 7 h, 12 h, and 24 h after administration. LC-MS/MS analysis method was used to detect contents of different insulin analogues. A metabolic kinetic data analysis software WinNonlin 7.0 was used to compile statistics of plasma concentration data, and a non-compartmental model method (NCA) was used to calculate pharmacokinetic parameters (Table 1). Results in Table 1 indicated that peak times of drugs in each group of animals were similar, i.e., 0.5-1 hour. Half-lives of L6-GFA16-insulins were 3-4 times that of recombinant human insulins. Exposure time of the drugs in vivo was prolonged and exposure doses were increased.

TABLE 1

| Main pharmacokinetic parameters in each group of animals | | | | | | | | | | | |
|---|---|---|---|---|---|---|---|---|---|---|---|
| Group | Rat number | Dose(mg/kg) | Kel(1/h) | Tmax(h) | Cmax(ng/mL) | AUC0-t(ng · h/mL) | AUC0-∞(ng · h/mL) | t1/2 (h) | V(mL/kg) | Cl(mL/h/kg) |
| Reference substance | 1 | 0.45 | 1.47 | 0.5 | 234 | 303 | 307 | 0.471 | 995 | 1465 |
| | 2 | 0.45 | 1.46 | 1 | 293 | 498 | 509 | 0.475 | 606 | 885 |
| | 3 | 0.45 | 1.23 | 1 | 201 | 359 | 373 | 0.564 | 980 | 1205 |
| Test substance 1 | 4 | 0.45 | 0.38 | 1 | 178 | 778 | 788 | 1.81 | 149 | 571 |
| | 5 | 0.45 | 20.409 | 0.5 | 171 | 677 | 683 | 1.69 | 51611 | 659 |
| | 6 | 0.45 | 0.454 | 1 | 192 | 826 | 831 | 1.53 | 1192 | 541 |

solution was added at a final concentration of 5 mM to induce the expression of a fusion protein. The culture solution was cultured for 16-20 hours, and then collected by centrifugation (10000 rpm, 5 min, 4° C.).

The amino acid sequence of SEQ ID NO: 12: MVSKGEELFTGVTYKTRAEVKFEGDTLVNRIELKGIDFENLYFQGDDDDKHAE GTFTSDVSSYLEGQAAKEFIAWLVKGRG, wherein the 70th K was a lysine to which a butynyloxycarbonyl group was covalently attached.

The fusion proteins were expressed in the form of insoluble "inclusion bodies". In order to release the inclusion bodies, the *E. coli* cells were disrupted with a high-pressure homogenizer. Cell debris and soluble *E. coli* host proteins were removed by centrifugation at 5000 g. The inclusion bodies were washed with a solution containing TWEEN80 (polysorbate 80), EDTA, and NaCl, and then washed with pure water 1-2 times. The washed inclusion bodies were dissolved in 7.5M urea, which contained 2-10 mM β-mercaptoethanol with a pH of 10.5-11.5, so that the concentration of a total protein after a dissolution reached 10-25 mg/mL. The sample was diluted 5-10 times, maintained between 4-8° C., and routinely folded for 14-30 hours under the pH condition of 10.5-11.7. After a clarification of a refolding solution, the fusion protein was separated and purified with weak anion packings under the pH condition of 9.0, and a purity of a target protein reached 80% confirmed by electrophoresis. The sample was eluted with high salt. After desalting, an enzyme digestion was performed with enterokinase for 10-20 hours at 25° C., and the pH value was maintained between 8.0-9.0. Reversed-phase HPLC analysis results showed that a yield of the enzyme digestion step was higher than 90%. A GLP-1 analog obtained after the enzyme digestion with enterokinase was named butynyloxycarbonyl-lysine-GLP-1. After the enzyme digestion, it was purified by hydrophobic packings to extract butynyloxycarbonyl-lysine-GLP-1, and the purity thereof confirmed by electrophoresis reached 90%.

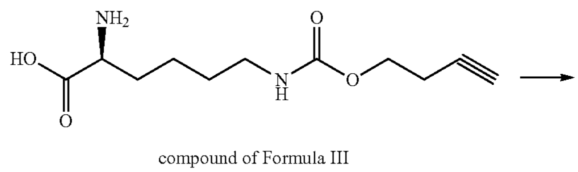

compound of Formula III

-continued

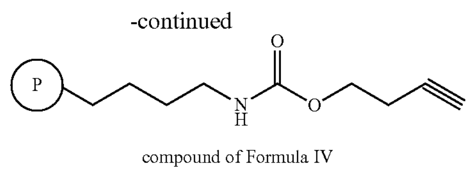

compound of Formula IV

Example 6 Synthesis of L0-GFA16-GLP-1 (n is 14)

Since a fatty acid acyl compound had an azide group, a GLP-1 protein with a terminal alkyne was introduced using the principle of "click chemistry", and the alkyne reacted with the azide to generate a 1,2,3-triazole ring, forming a cross-link. 4 μL of copper sulfate (50 μM) was added to a clean 1.5 mL centrifuge tube, then 3 μL of BTTAA (300 μM) was added and 10 μL of a compound IV (N-(butynyloxy-carbonyl)-lysine-GLP-1 protein) (approximately 5 μM) which was prepared in Example 5 was added in order. At this time, the solution could be diluted to an appropriate volume or protein concentration. To this solution, 1 μL of L0-GFA16 (1 mM) was added, and 2 μL of sodium ascorbate (2.5 mM) was added to initiate the reaction. After about 1 hour at room temperature, 5 μL of SDS-PAGE sample buffer was added and heated to 100° C. for 10 minutes. An analysis of the solution was completed by 12% SDS-PAGE. A gel was recovered, then analyzed by gel imaging and fluorescence analysis, and then stained with Coomassie brilliant blue.

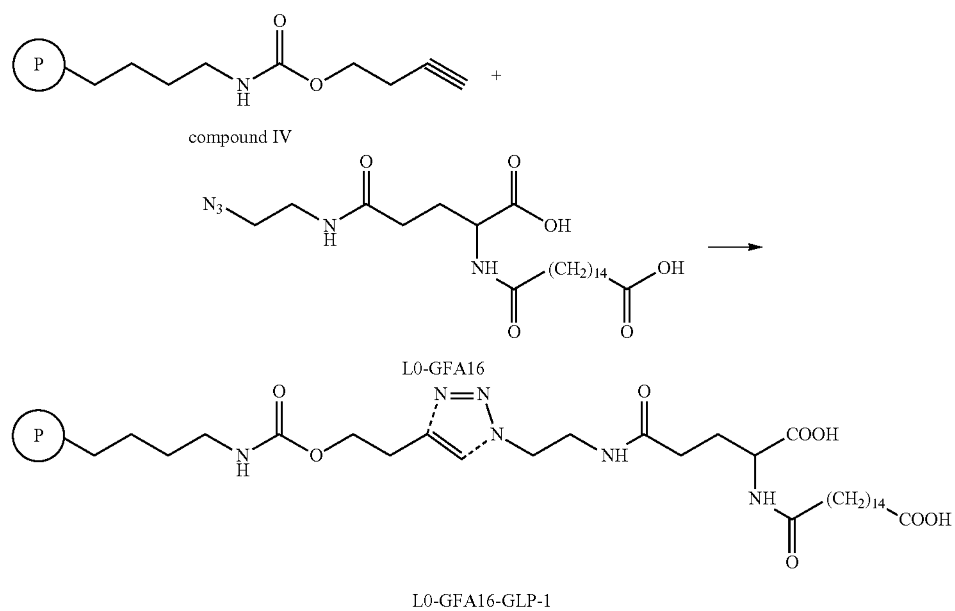

compound IV

L0-GFA16

L0-GFA16-GLP-1

Example 7 Synthesis of L2-GFA16-GLP-1, L3-GFA16-GLP-1, L4-GFA16-GLP-1, L5-GFA16-GLP-1 and L6-GFA16-GLP-1 (n is 14)

4 μL of copper sulfate (50 μM) was added to a clean 1.5 mL centrifuge tube, then 3 μL of BTTAA (300 μM) was added and 10 μL of a compound IV (N-(butynyloxycarbonyl)-lysine-GLP-1 protein) (approximately 5 μM) which was prepared in Example 5 was added in order. At this time, it may be necessary to add water to dilute the solution to a proper volume or protein concentration. To this solution, 1 μL of L2-GFA16 (1 mM) was added, and 2 μL of sodium ascorbate (2.5 mM) was added to initiate the reaction. After about 1 hour at room temperature, 5 μL of SDS-PAGE sample buffer was added and heated to 100° C. for 10 minutes. An analysis of the solution was completed by 12% SDS-PAGE. A gel was recovered, then analyzed by gel imaging and fluorescence analysis, and then stained with Coomassie brilliant blue.

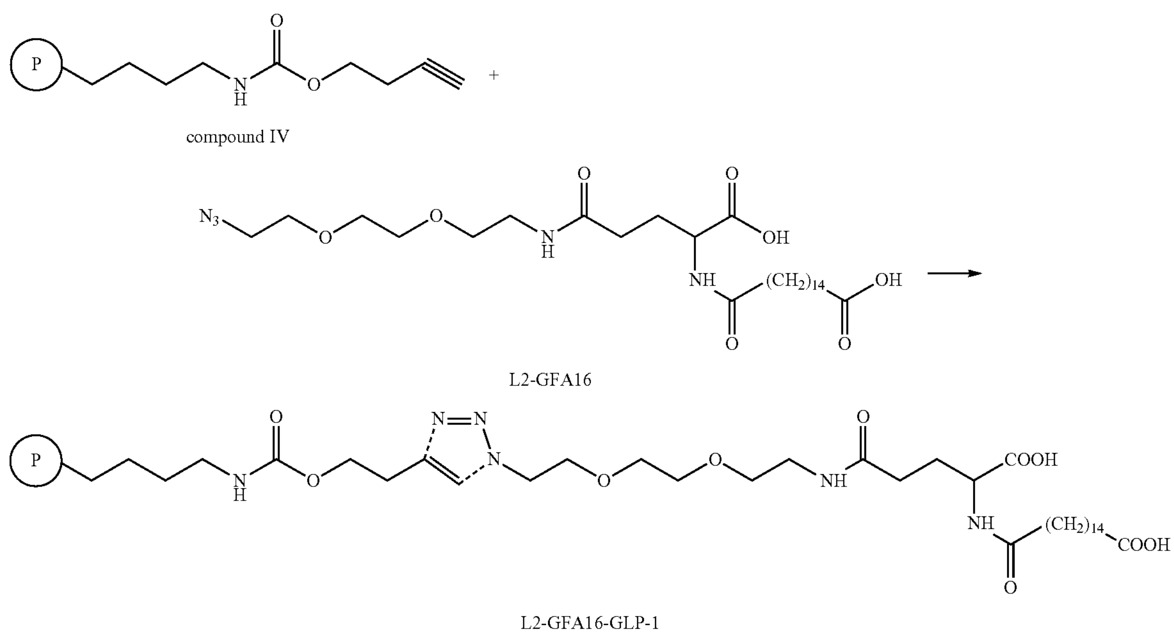

compound IV

L2-GFA16

L2-GFA16-GLP-1

Similarly, the compound IV prepared in Example 5 and L3-GFA16, L4-GFA16, L5-GFA16, and L6-GFA16 were respectively used to complete a click reaction to obtain the following products, and their structures were shown below.

results showed that a yield of the enzyme digestion step was higher than 90%. A PTH analog obtained after the enzyme digestion with enterokinase was named butynyloxycarbonyl-lysine-PTH. After the enzyme digestion, it was purified

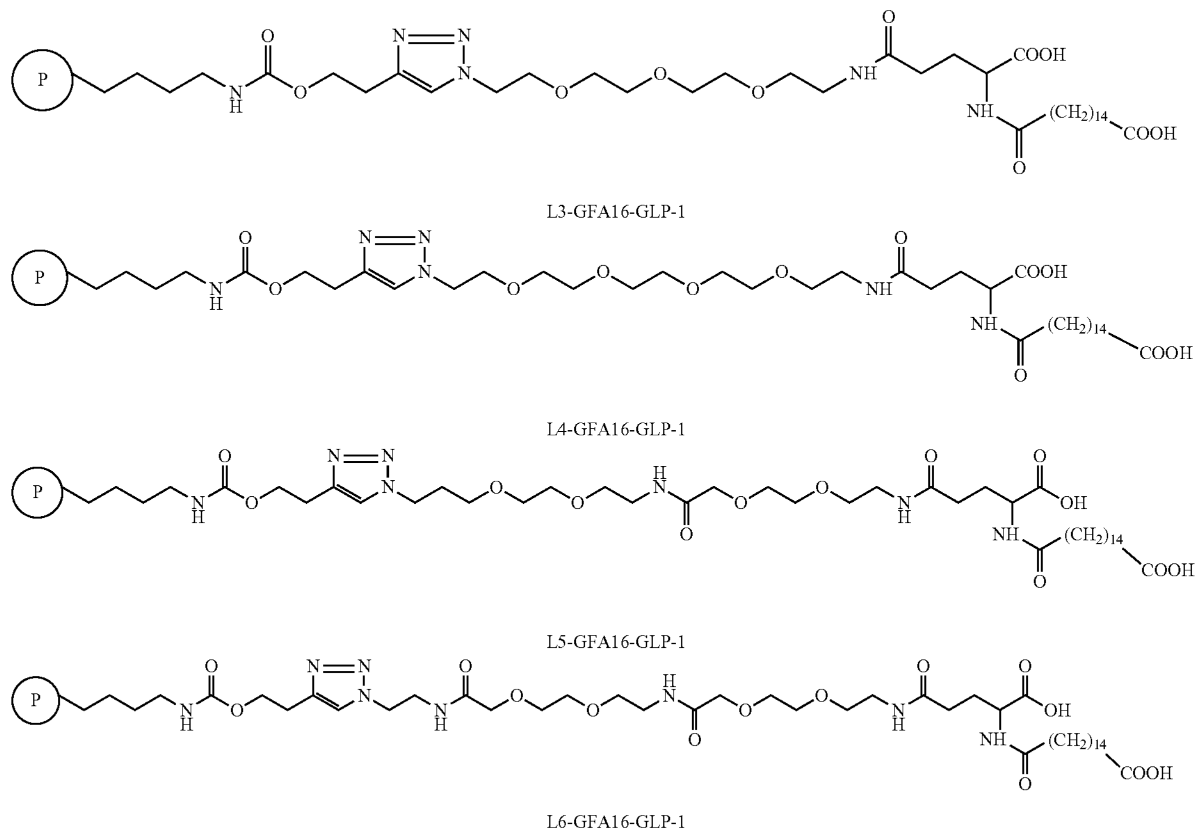

L3-GFA16-GLP-1

L4-GFA16-GLP-1

L5-GFA16-GLP-1

L6-GFA16-GLP-1 centrifugation (10000 rpm, 5 min, 4° C.).

The amino acid sequence of SEQ ID NO: 13: MVSKGEELFTGVTYKTRAEVKFEGDTLVNRIELKGIDFENLYFQGDDDDKSVSE IQLMHNLGRHLNSMERVEWLRKRLQDVHNF, wherein the 76th K was a lysine to which a butynyloxycarbonyl group was covalently attached.

The fusion proteins were expressed in the form of insoluble "inclusion bodies". In order to release the inclusion bodies, the *E. coli* cells were disrupted with a high-pressure homogenizer. Cell debris and soluble *E. coli* host proteins were removed by centrifugation at 5000 g. The inclusion bodies were washed with a solution containing TWEEN80 (polysorbate 80), EDTA, and NaCl, and then washed with pure water 1-2 times. The washed inclusion bodies were dissolved in 7.5M urea, which contained 2-10 mM β-mercaptoethanol with a pH of 10.5-11.5, so that the concentration of a total protein after a dissolution reached 10-25 mg/mL. The sample was diluted 5-10 times, maintained between 4-8° C., and routinely folded for 14-30 hours under the pH condition of 10.5-11.7. After a clarification of a refolding solution, the fusion protein was separated and purified with weak anion packings under the pH condition of 9.0, and a purity of a target protein reached 80% confirmed by electrophoresis. The sample was eluted with high salt. After desalting, an enzyme digestion was performed with enterokinase for 10-20 hours at 25° C., and the pH value was maintained between 8.0-9.0. Reversed-phase HPLC analysis by hydrophobic packings to extract butynyloxycarbonyl-lysine-PTH, and the purity thereof confirmed by electrophoresis reached 90%.

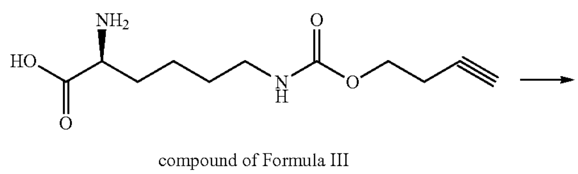

compound of Formula III

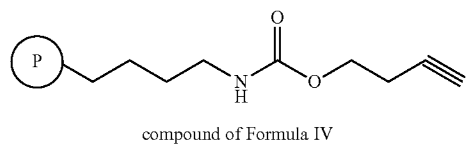

compound of Formula IV

Methods were the same as in Examples 6 and 7. The PTH proteins containing N-(butynyloxycarbonyl)-lysine were substituted for the GLP-1 proteins containing N-(butynyloxycarbonyl)-lysine to synthesize L0-GFA16-PTH, L2-GFA16-PTH, L3-GFA16-PTH, L4-GFA16-PTH, L5-GFA16-PTH and L6-GFA16-PTH.

The invention claimed is:

1. A method for preparing a polypeptide derivative, comprising the following steps:

(1) cultivating a strain containing a polypeptide coding sequence in the presence of a compound of Formula III, a pyrrolysyl-tRNA synthetase and a homologous associated tRNA thereof, wherein a lysine within the polypeptide derivative coding sequence is replaced with TAG, thereby producing a compound of Formula IV; then isolating or purifying the compound of Formula IV from cell culture of the strain; and

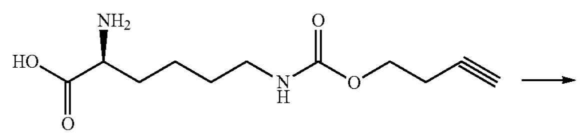

compound of Formula III

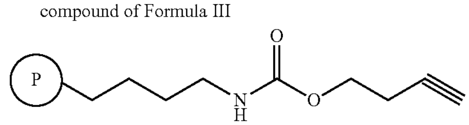

compound of Formula IV wherein

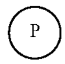

is an insulin, glucagon-like peptide-1 (GLP-1) or parathyroid hormone (PTH);

wherein the strain is *E. coli* Top10 strain;

wherein the compound of Formula IV is expressed in a form of insoluble inclusion bodies;

wherein the insoluble inclusion bodies consist of the amino acid sequence of SEQ ID NO: 11, SEQ ID NO: 12 or SEQ ID NO: 13;

(2) undertaking a reaction between the compound of Formula IV and a compound of Formula V in an inert solvent, compound of Formula V

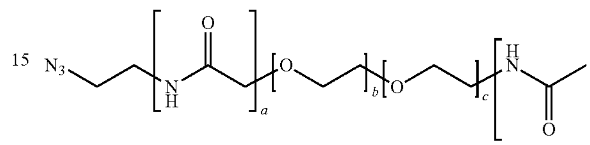

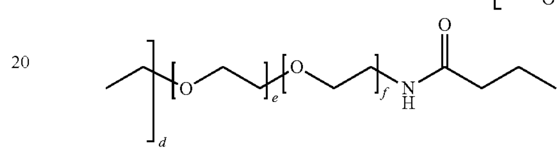

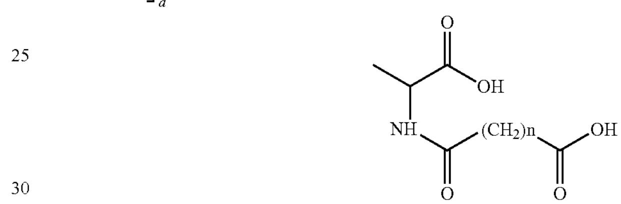

wherein a, b, c, d, e and f are independent integers selected from 0 to 10; n is 14 in Formula V;

thereby producing the polypeptide derivative selected from the group consisting of:

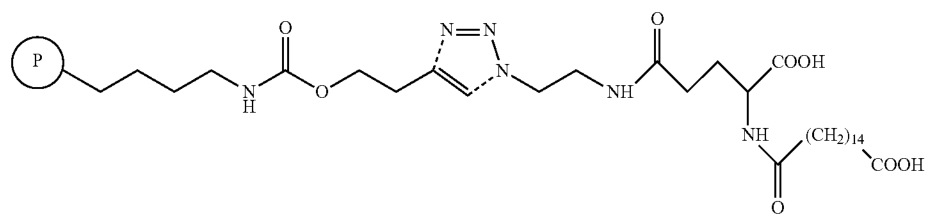

(when a, b, c, d, e and f are all 0 in Formula V),

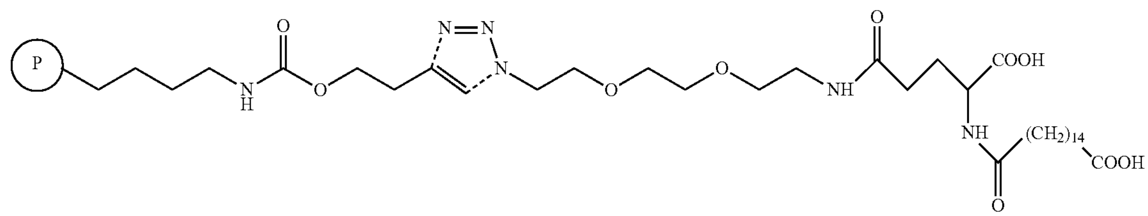

(when a, b, c, d and e are all 0, and f is 2 in Formula V),

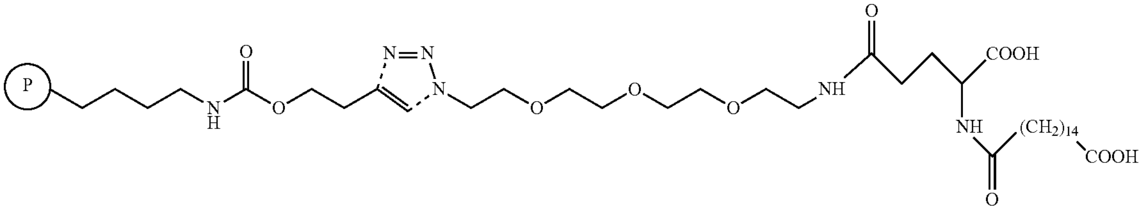

(when a, b, c, d and e are all 0, and f is 3 in Formula V),

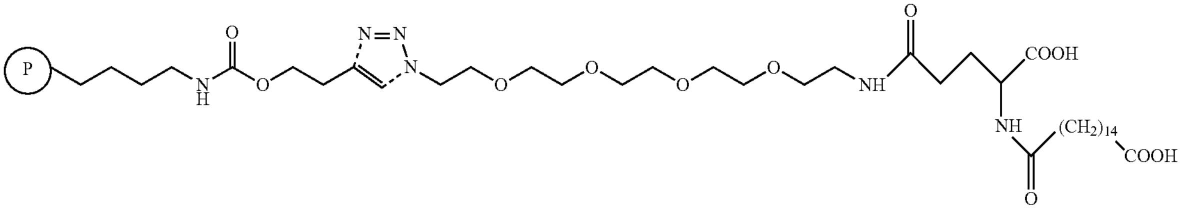

(when a, b, c, d and e are all 0, and f is 4 in Formula V),

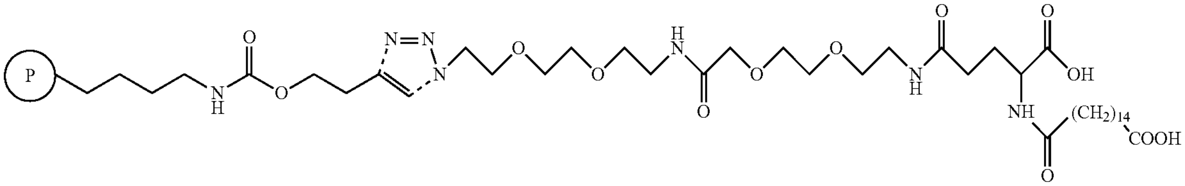

(when a is 0, and b, c, d, e and f are all 1 in Formula V), and

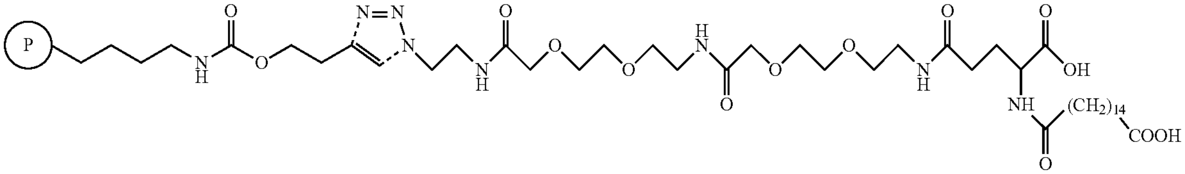

(when a, b, c, d, e and f are all 1 in Formula V), wherein

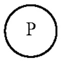

is an insulin, glucagon-like peptide-1 (GLP-1) or parathyroid hormone (PTH).

2. The method of claim 1, wherein an A chain of the insulin consists of the amino acid sequence of SEQ ID NO: 1 or 2;

a B chain of the insulin consists of the amino acid sequence of SEQ ID NO: 3, 4, 5 or 6;

the GLP-1 consists of the amino acid sequence of any one of SEQ ID NO: 7-9; or the PTH consists of the amino acid sequence of SEQ ID NO: 10.

3. The method of claim 1, wherein the method further comprises a step of isolating the polypeptide derivative from fermentation products.

4. The method of claim 1, wherein the

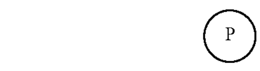

is human insulin, and the method further comprises the following steps:

(i) disrupting *E. coli* cells using a high-pressure homogenizer, removing cell debris and soluble *E. coli* host proteins from the disrupted cell mixture by centrifugation at 5000 g, washing insoluble inclusion bodies obtained from the centrifuged mixture with a solution containing polysorbate 80, ethylenediaminetetraacetic acid (EDTA) and NaCl, and then washing the insoluble inclusion bodies with purified water 1-2 times; wherein the insoluble inclusion bodies consist of the amino acid sequence of SEQ ID NO: 11;

(ii) dissolving washed insoluble inclusion bodies in 7.5M urea, wherein the 7.5M urea contains 2-10 mM β-mercaptoethanol and has a pH of 10.5-11.5, such that a total protein concentration of a dissolved inclusion body sample reaches 10-25 mg/mL;

(iii) diluting the dissolved inclusion body sample 5-10 times, maintaining the diluted sample at 4-8° C. and allowing it to fold for 14-30 hours under a pH of 10.5-11.7, performing enzyme digestion on the folded sample using trypsin and carboxypeptidase B for 10-20 hours at 18-25° C. while maintaining pH value of a digestion system between 8.0-9.5, and adding 0.45M ammonium sulfate to a digestion mixture to terminate the enzyme digestion;

(iv) naming an insulin analog obtained after the enzyme digestion as butynyloxycarbonyl-lysine-human insulin, clarifying the butynyloxycarbonyl-lysine-human insulin sample via membrane filtration, and subjecting the clarified sample to initial purification by hydrophobic chromatography to obtain a crude extract of butynyloxycarbonyl-lysine-human insulin; and (v) purifying the crude extract using reverse-phase chromatography, and obtaining butynyloxycarbonyl-lysine-human insulin with a purity higher than 99%.

5. The method of claim 1, wherein the

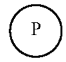

is GLP-1, and the method further comprises the following steps:

(i) disrupting *E. coli* cells using a high-pressure homogenizer, removing cell debris and soluble *E. coli* host proteins from the disrupted cell mixture by centrifugation at 5000 g, washing insoluble inclusion bodies obtained from the centrifuged mixture with a solution containing polysorbate 80, ethylenediaminetetraacetic acid (EDTA) and NaCl, and then washing the insoluble inclusion bodies with purified water 1-2 times; wherein the insoluble inclusion bodies consist of the amino acid sequence of SEQ ID NO: 12;

(ii) dissolving washed insoluble inclusion bodies in 7.5M urea, wherein the 7.5M urea contains 2-10 mM β-mercaptoethanol and has a pH of 10.5-11.5, such that a total protein concentration of a dissolved inclusion body sample reaches 10-25 mg/mL;

(iii) diluting the dissolved inclusion body sample 5-10 times, maintaining the diluted sample at 4-8° C. and allowing it to fold for 14-30 hours under a pH of 10.5-11.7, clarifying a refolding solution, and separating and purifying a butynyloxycarbonyl-lysine-GLP-1 uncleaved precursor using weak anion exchange chromatography under a pH of 9.0;

(iv) eluting the butynyloxycarbonyl-lysine-GLP-1 uncleaved precursor with a high-salt solution, desalting the butynyloxycarbonyl-lysine-GLP-1 uncleaved precursor, and performing enzyme digestion on the desalted butynyloxycarbonyl-lysine-GLP-1 uncleaved precursor using enterokinase for 10-20 hours at 25° C. while maintaining pH value between 8.0-9.0; and (v) naming a GLP-1 analog obtained after the enzyme digestion as butynyloxycarbonyl-lysine-GLP-1, and purifying the butynyloxycarbonyl-lysine-GLP-1 using hydrophobic chromatography to extract purified butynyloxycarbonyl-lysine-GLP-1, wherein a purity of the purified butynyloxycarbonyl-lysine-GLP-1 reaches 90% as confirmed by electrophoresis.

6. The method of claim 1, wherein the

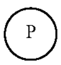

is PTH, and the method further comprises the following steps:

(i) disrupting *E. coli* cells using a high-pressure homogenizer, removing cell debris and soluble *E. coli* host proteins from the disrupted cell mixture by centrifugation at 5000 g, washing insoluble inclusion bodies obtained from the centrifuged mixture with a solution containing polysorbate 80, ethylenediaminetetraacetic acid (EDTA) and NaCl, and then washing the insoluble inclusion bodies with purified water 1-2 times; wherein the insoluble inclusion bodies consist of the amino acid sequence of SEQ ID NO: 13;

(ii) dissolving washed insoluble inclusion bodies in 7.5M urea, wherein the 7.5M urea contains 2-10 mM β-mercaptoethanol and has a pH of 10.5-11.5, such that a total protein concentration of a dissolved inclusion body sample reaches 10-25 mg/mL;

(iii) diluting the dissolved inclusion body sample 5-10 times, maintaining the diluted sample at 4-8° C. and allowing it to fold for 14-30 hours under a pH of 10.5-11.7, clarifying a refolding solution, and separating and purifying a butynyloxycarbonyl-lysine-PTH uncleaved precursor using weak anion exchange chromatography under a pH of 9.0;

(iv) eluting the butynyloxycarbonyl-lysine-PTH uncleaved precursor with a high-salt solution, desalting the butynyloxycarbonyl-lysine-PTH uncleaved precursor, and performing enzyme digestion on the desalted butynyloxycarbonyl-lysine-PTH uncleaved precursor using enterokinase for 10-20 hours at 25° C. while maintaining pH value between 8.0-9.0; and (v) naming a PTH analog obtained after the enzyme digestion as butynyloxycarbonyl-lysine-PTH, and purifying the butynyloxycarbonyl-lysine-PTH using hydrophobic chromatography to extract purified butynyloxycarbonyl-lysine-PTH, wherein a purity of the purified butynyloxycarbonyl-lysine-PTH reaches 90% as confirmed by electrophoresis.

* * * * *

SEQUENCE LISTING

```
<160> NUMBER OF SEQ ID NOS: 19

<210> SEQ ID NO 1
<211> LENGTH: 21
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino Acid Sequence of A Chain of an Insulin

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20


<210> SEQ ID NO 2
<211> LENGTH: 21
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino Acid Sequence of A Chain of an Insulin

<400> SEQUENCE: 2

Gly Ile Val Glu Gln Cys Cys Thr Ser Ile Cys Ser Leu Tyr Gln Leu
1               5                   10                  15

Glu Asn Tyr Cys Gly
            20


<210> SEQ ID NO 3
<211> LENGTH: 30
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino Acid Sequence of B Chain of an Insulin

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30


<210> SEQ ID NO 4
<211> LENGTH: 29
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino Acid Sequence of B Chain of an Insulin

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25
```

-continued

<210> SEQ ID NO 5
<211> LENGTH: 30
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino Acid Sequence of B Chain of an Insulin

<400> SEQUENCE: 5

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30
```

<210> SEQ ID NO 6
<211> LENGTH: 30
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino Acid Sequence of B Chain of an Insulin

<400> SEQUENCE: 6

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30
```

<210> SEQ ID NO 7
<211> LENGTH: 31
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino Acid Sequence of GLP-1

<400> SEQUENCE: 7

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

<210> SEQ ID NO 8
<211> LENGTH: 31
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino Acid Sequence of GLP-1

<400> SEQUENCE: 8

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30
```

<210> SEQ ID NO 9
<211> LENGTH: 31
<212> TYPE: PRT

-continued

```
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino Acid Sequence of GLP-1
<220> FEATURE:
<221> NAME/KEY: misc_feature
<222> LOCATION: (2)..(2)
<223> OTHER INFORMATION: Xaa=2-aminoisobutyric acid (Aib)

<400> SEQUENCE: 9

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30


<210> SEQ ID NO 10
<211> LENGTH: 34
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino Acid Sequence of PTH

<400> SEQUENCE: 10

Ser Val Ser Glu Ile Gln Leu Met His Asn Leu Gly Arg His Leu Asn
1               5                   10                  15

Ser Met Glu Arg Val Glu Trp Leu Arg Lys Arg Leu Gln Asp Val His
            20                  25                  30

Asn Phe


<210> SEQ ID NO 11
<211> LENGTH: 103
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino Acid Sequence of a Butynyloxycarbonyl-
      lysine

<400> SEQUENCE: 11

Met Val Ser Lys Gly Glu Glu Leu Phe Thr Gly Val Thr Tyr Lys Thr
1               5                   10                  15

Arg Ala Glu Val Lys Phe Glu Gly Asp Asp Asp Asp Asp Lys Thr Leu
            20                  25                  30

Val Asn Arg Ile Glu Leu Lys Gly Ile Asp Phe Glu Asn Leu Tyr Phe
        35                  40                  45

Gln Gly Arg Phe Val Asn Gln His Leu Cys Gly Ser His Leu Val Glu
    50                  55                  60

Ala Leu Tyr Leu Val Cys Gly Glu Arg Gly Phe Phe Tyr Thr Pro Lys
65                  70                  75                  80

Thr Arg Gly Ile Val Glu Gln Cys Cys Thr Ser Ile Cys Ser Leu Tyr
                85                  90                  95

Gln Leu Glu Asn Tyr Cys Asn
            100


<210> SEQ ID NO 12
<211> LENGTH: 81
<212> TYPE: PRT
```

-continued

<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino Acid Sequence of a Butynyloxycarbonyl-
lysine

<400> SEQUENCE: 12

Met Val Ser Lys Gly Glu Glu Leu Phe Thr Gly Val Thr Tyr Lys Thr
1 5 10 15

Arg Ala Glu Val Lys Phe Glu Gly Asp Thr Leu Val Asn Arg Ile Glu
20 25 30

Leu Lys Gly Ile Asp Phe Glu Asn Leu Tyr Phe Gln Gly Asp Asp Asp
35 40 45

Asp Lys His Ala Glu Gly Thr Phe Thr Ser Asp Val Ser Ser Tyr Leu
50 55 60

Glu Gly Gln Ala Ala Lys Glu Phe Ile Ala Trp Leu Val Lys Gly Arg
65 70 75 80

Gly

<210> SEQ ID NO 13
<211> LENGTH: 84
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino Acid Sequence of a Butynyloxycarbonyl-
lysine

<400> SEQUENCE: 13

Met Val Ser Lys Gly Glu Glu Leu Phe Thr Gly Val Thr Tyr Lys Thr
1 5 10 15

Arg Ala Glu Val Lys Phe Glu Gly Asp Thr Leu Val Asn Arg Ile Glu
20 25 30

Leu Lys Gly Ile Asp Phe Glu Asn Leu Tyr Phe Gln Gly Asp Asp Asp
35 40 45

Asp Lys Ser Val Ser Glu Ile Gln Leu Met His Asn Leu Gly Arg His
50 55 60

Leu Asn Ser Met Glu Arg Val Glu Trp Leu Arg Lys Arg Leu Gln Asp
65 70 75 80

Val His Asn Phe

<210> SEQ ID NO 14
<211> LENGTH: 4
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino Acid Sequence of a Motif

<400> SEQUENCE: 14

Tyr Thr Pro Lys
1

<210> SEQ ID NO 15
<211> LENGTH: 5
<212> TYPE: PRT
<213> ORGANISM: Artificial Sequence -continued
<220> FEATURE:
<223> OTHER INFORMATION: synthesized
<220> FEATURE:
<221> NAME/KEY: misc_feature
<223> OTHER INFORMATION: Amino Acid Sequence of a Motif

<400> SEQUENCE: 15

Tyr Thr Asp Lys Thr
1               5

<210> SEQ ID NO 16
<211> LENGTH: 5
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino Acid Sequence of a Motif

<400> SEQUENCE: 16

Tyr Thr Pro Lys Thr
1               5

<210> SEQ ID NO 17
<211> LENGTH: 5
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino Acid Sequence of a Motif

<400> SEQUENCE: 17

Tyr Thr Lys Pro Thr
1               5

<210> SEQ ID NO 18
<211> LENGTH: 5
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino Acid Sequence of a Motif

<400> SEQUENCE: 18

Ala Ala Lys Glu Phe
1               5

<210> SEQ ID NO 19
<211> LENGTH: 5
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino Acid Sequence of a Motif

<400> SEQUENCE: 19

Leu Arg Lys Arg Leu
1               5